United States Patent
Coupland

(10) Patent No.: US 9,403,042 B2
(45) Date of Patent: Aug. 2, 2016

(54) COMPOSITION FOR TREATMENT OF SKIN

(75) Inventor: Keith Coupland, South Cliffe (GB)

(73) Assignee: Seeds Group, LP, New York, NY (US)

(*) Notice: Subject to any disclaimer, the term of this patent is extended or adjusted under 35 U.S.C. 154(b) by 412 days.

(21) Appl. No.: 13/147,248

(22) PCT Filed: Feb. 5, 2010

(86) PCT No.: PCT/GB2010/000215
§ 371 (c)(1),
(2), (4) Date: Aug. 19, 2011

(87) PCT Pub. No.: WO2010/089566
PCT Pub. Date: Aug. 12, 2010

(65) Prior Publication Data
US 2011/0293751 A1     Dec. 1, 2011

(30) Foreign Application Priority Data
Feb. 6, 2009 (GB) .................... 0902040.5

(51) Int. Cl.
| A61K 36/30 | (2006.01) |
| A61K 36/185 | (2006.01) |
| A61Q 19/08 | (2006.01) |
| A61K 8/36 | (2006.01) |
| A61K 8/92 | (2006.01) |

(52) U.S. Cl.
CPC ................ *A61Q 19/08* (2013.01); *A61K 8/361* (2013.01); *A61K 8/922* (2013.01)

(58) Field of Classification Search
None
See application file for complete search history.

(56) References Cited

U.S. PATENT DOCUMENTS

| 6,340,485 | B1* | 1/2002 | Coupland et al. ............. 424/776 |
| 2003/0175914 | A1* | 9/2003 | Baldenius et al. ............ 435/134 |
| 2004/0161435 | A1 | 8/2004 | Gupta |
| 2007/0280898 | A1 | 12/2007 | Riddle |
| 2008/0045594 | A1* | 2/2008 | Piccirilli et al. .............. 514/558 |
| 2008/0213357 | A1 | 9/2008 | Hebard et al. |

FOREIGN PATENT DOCUMENTS

| EP | 0920300 | 6/1999 |
| FR | 2902334 | 12/2007 |
| JP | 2001253817 | 9/2001 |
| RO | 118256 | 4/2003 |
| WO | 97/46220 | 12/1997 |
| WO | 02/092073 | 11/2002 |
| WO | 2004/022034 | 3/2004 |
| WO | 2007/004229 | 1/2007 |
| WO | 2008/000974 | 1/2008 |
| WO | 2010/013015 | 2/2010 |

OTHER PUBLICATIONS

International Search Report for International Application No. PCT/GB2010/000215, dated Feb. 4, 2011.

* cited by examiner

*Primary Examiner* — Chris R Tate
*Assistant Examiner* — Deborah Davis
(74) *Attorney, Agent, or Firm* — Edward J. Baba

(57) ABSTRACT

The present invention provides a composition comprising stearidonic acid (or an ester thereof) derived for example from *Echium* oil, and an additional lipid (derived for example from *calendula* oil) which enhances the pro-collagen effects of stearidonic acid. The composition is useful in reducing visible signs of aging of human or animal skin or a method of wound healing.

6 Claims, 6 Drawing Sheets

COMPOSITION FOR TREATMENT OF SKIN

The present invention relates to a composition for topical application to the human or animal body. In particular, it relates to compositions containing naturally occurring plant seed oils to stimulate collagen synthesis in skin cells. Such compositions are useful in the treatment of skin and in wound healing.

Most plant seed oils (lipids) are triglyceride esters of fatty acids and glycerol. The fatty acids may be saturated, mono-unsaturated or poly-unsaturated. The plant seed oils that are of value in the treatment of skin conditions, by stimulating collagen production in skin cells, are those containing poly-unsaturated fatty acids. Fatty acids are aliphatic monocarboxylic acids which occur naturally in animal or vegetable fats or oils in the form of esters particularly triglyceride esters. Because of their perceived usefulness in for example human nutrition, a great deal of effort has been put into extracting triglyceride esters containing poly-unsaturated fatty acids from their natural sources.

Stearidonic acid (SDA) is a polyunsaturated fatty acid of the n3 family which is described in the conventional nomenclature as C18:4n3. It can be found in the form of a triester of glycerol (or triglyceride) in the oils of blackcurrant, redcurrant and gooseberry pips. WO 97/46220 (Croda International Plc) discloses that SDA triglyceride can be sourced from oil extracted from the seeds of the Boraginaceae plant family and that the oil itself can be used in dietetic, cosmetic and healthcare products, without the need for additional treatment or purification. A particularly rich source of SDA is the seeds of the genus *Echium*.

U.S. Pat. No. 6,340,485 (Croda International Plc) discloses a composition comprising from 1 to 20% by weight of an oil extracted from the seeds of Boraginaceae plant species (particularly the *Echium* species) comprising from 5 to 20 SDA triglyceride an 80 to 95% of other fatty acid triglycerides. The composition is said to be particularly suited for oral or topical administration and for dietary, cosmetic, pharmaceutical and healthcare use. In particular, the composition is said to be especially advantageous for use in treating skin inflammation and particularly sunburn. Although it is admitted that the pathogenesis of sunburn is not completely understood, it is postulated that the release of inflammatory mediators including eicosanoids and cytokines (which can be metabolised from SDA) seems to be important.

A number of other prior art references disclose the use of *Echium* oil in compositions for treating skin, for example: WO 2008/00074 A2 (L'Occitane); US 2008/0213357 A1 (Hebard); and WO 02/092073 A1 (Martek Biosciences Boulder Corporation). A composition comprising the active ingredients of *Echium* oil (stearidonic acid and gamma-linolenic acid) is also disclosed in EP 0 460 848 A1 (Efamol Holdings Plc.).

US 2004/0161435 A1 (Gupta) discloses a cosmetic mask composition which promotes excess fat reduction, cellulite control or muscle and skin toning benefits. An exemplary composition comprises extracts of rosemary, marigold, sage, ginseng, St. John's wart and ruscus as active ingredients.

Marigold extract is also disclosed as an active ingredient in cosmetic compositions to fight against the signs of skin aging in the following prior art references: FR 2902334 A1 (Laboratoire Nuxe); JP 2001253817 A (Nagase); and WO 2004/022034 A1 (Dermaphyt).

RO 118256 B (Farmec SA) discloses an anti-wrinkle cosmetic cream comprising inter alia an extract from the leaves and flowering stalks of *Calendula*. Oil (such as peanut oil) is used for the extraction, but it is not believed that the composition comprises *Calendula* oil in the sense of an oil produced from *Calendula* seeds.

Skin aging is the result of two distinct processes; extrinsic (caused by environmental factors such as UVA/UVB exposure, lifestyle, tobacco smoking, excessive alcohol intake and diet) and intrinsic or chronological aging where genetic factors are involved. The visible result of skin aging is loss of skin tone and elasticity, dehydration, skin roughness, age spots, lines and wrinkles. It is known that a major factor involved in the production of skin sagging, lines and wrinkles is the chronological reduction in skin collagen. In addition environmental factors can stimulate the production of proteolytic enzymes involved in collagen breakdown.

In a first aspect of the present invention there is provided a composition for topical application to the human or animal body comprising stearidonic acid, or an ester thereof, and an additional lipid which enhances the pro-collagen effects of stearidonic acid.

In a preferred embodiment said additional lipid is a conjugated octadecatrienoic acid (CODTA) or an ester thereof. The best known naturally occurring CODTAs are tabulated below:

| CODTA | Configuration | Source |
| --- | --- | --- |
| Calendic acid | 8t10t12c-18:3 | *Calendula officinalis* |
| Catalpic acid | 9t11t13c-18:3 | *Catalpa ovata* |
| α-Eleostearic acid | 9c11t13t-18:3 | *Aleurites fordii* |
| Jacaric acid | 8c10t12c-18:3 | *Jacaranda mimosifolia* |
| Punicic acid | 9c11t13c-18:3 | *Punica granatum* |

Preferably, the stearidonic acid is provided by oil extracted from the seeds of the Boraginaceae plant family, and most preferably from the *Echium* species *Echium* plantagineum. The oil may be present in an amount from 0.1% to 10% w/w, preferably about 4.95% w/w.

The additional lipid is preferably present is an amount from 0.005% to 1% w/w, more preferably from 0.01% to 0.1% w/w, most preferably about 0.05% w/w.

The compositions of the present invention may also comprise a physiologically acceptable carrier. For example, they may additionally comprise one or more of a moisturiser, an emollient, an emulsifier, a preservative, a dispersant, a viscosity modifier, a herbal extract, a solvent, a chelating agent, an antioxidant, vitamin C, an ester of vitamin C, ascorbyl palmitate, magnesium ascorbyl phosphate, a water-proofing agent, a pH adjuster, a perfume, and an aminoacid, peptide or protein.

The compositions may be formulated as solids, liquids, aerosols, creams, emulsions, gels or in capsule form.

In a second aspect of the invention there is provided a method of reducing visible signs of aging of human or animal skin comprising applying to said skin any of said compositions as defined above in combination with a physiologically acceptable carrier.

In a third aspect of the invention there is provided a method of healing wounds in a human or animal body comprising applying to the locus of the wound any of said compositions as defined above in combination with a physiologically acceptable carrier.

In accordance with a fourth aspect of the present invention, there is provided a composition comprising stearidonic acid (preferably provided in the form of *Echium* oil) or *calendula* oil or a mixture thereof for use in the stimulation of collagen synthesis in skin cells.

The surprising realisation of the present applicant is that *Echium* oil and *calendula* oil act alone (or in combination) to stimulate collagen synthesis in skin cells. Previously, this mechanism of action has not been known. The result of this inventive realisation is that the composition can be used as cosmetic products and also as components in wound dressings to accelerate wound healing.

It is important to note that the active ingredient is *calendula* oil and not *calendula* extract as employed in the prior art. The extract is a decoction of *calendula* flowers (usually in a vegetable oil such as sunflower seed oil or peanut oil) whereas the oil may be produced by grinding up the seeds of the *Calendula* plant and extracting the diminuted seed with a suitable solvent such as hexane or super critical carbon dioxide. Alternatively the oil may be obtained by simply cold pressing the *Calendula* seeds. *Calendula* extract does not contain calendic acid whereas *calendula* oil does.

In accordance with a further aspect of the present invention, there is provided a composition comprising stearidonic acid (preferably provided in the form of *Echium* oil) for use in the reduction of trans-epidermal water loss.

In accordance with yet a further aspect of the present invention, there is provided a composition comprising stearidonic acid (preferably provided in the form of *Echium* oil) for use in the reduction of skin wrinkles.

A number of preferred embodiments of the invention will now be described with reference to the following drawings, in which.

EXAMPLES

A] Formulations with *Echium* Oil

1. Moisturizing Lotion

Figure 1:
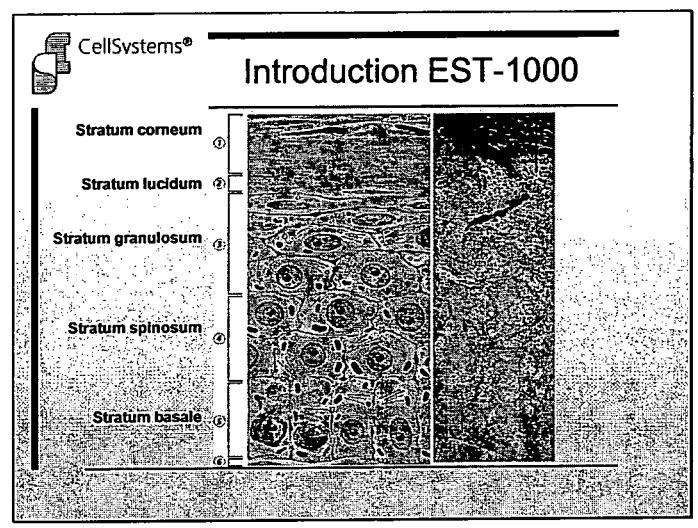
FIG. 1 is a diagram showing the EST-1000 epidermis model.

|  | % by weight |
| --- | --- |
| Caprylic/Capric Triglyceride | 8.0 |
| Nonionic Emulsifying Wax | 2.5 |
| Cetearyl Alcohol | 1.0 |
| Glyceryl Stearate non-emulsifiable (N/E) | 1.5 |
| *Echium* Oil | 1.0-4.0 |
| Water | to 100 |
| Carbomer - Carbopol 981 2% solution (B F Goodrich) | 10.0 |
| Glycerine | 2.0 |
| Triethanolamine | to pH 6.5-7.0 |
| Perfume, Preservative, Colour | qs |

Method

Heat oil phase and water phase separately to 65-70 Deg C. Add water phase to oil phase with stirring and cool. Add perfume, preservatives, colour and optional ingredients e.g. plant extracts at 35 Deg C.

2. Anti-Wrinkle Night Cream

| Phase A | |
| --- | --- |
| Ceteareth-25 | 2.0 |
| Ceteareth-6/Stearyl Alcohol | 2.0 |
| Mineral Oil | 8.0 |
| Cetearyl Ethylhexanoate | 7.0 |
| Glyceryl Stearate | 6.0 |
| Cetyl Alcohol | 1.0 |
| *Echium* oil | 1.0-5.0 |
| Phase B | |
| Water | to 100 |
| Panthenol, Propylene Glycol | 1.0 |
| Propylene Glycol | 3.0 |
| Sodium Lactate | 5.0 |
| Perfume, Preservative | qs |
| Phase C | |
| Caprylic/Capric Triglyceride, Acrylates Copolymer | 1.3 |

Method

Heat phases A and B separately to about 80 Deg C. Stir phase B into phase A and homogenize. Add phase C with stirring to phase A+B and homogenize. Cool to 40 Deg C.

3. Light Day Cream

| Dioctyl Succinate | 6.0 |
| --- | --- |
| Glyceryl Stearate, PEG100 | 4.0 |
| Nonionic Emulsifying Wax GP200 | 4.0 |
| *Echium* Oil | 4.0-8.0 |
| Water | to 100 |
| Carbomer (Carbopol 981, 2% aqueous solution) | 10.0 |
| Perfume, Preservative, Colour | qs |

Method

Heat oil and water phases separately to 65-70 Deg C. Add water phase to oil phase with stirring. Stir to cool adjusting pH to about 7 with triethanolamine at 60 Deg C.

4. Deep Wrinkle Treatment

| Phase A | |
| --- | --- |
| Cetearyl Alcohol, Dicetyl Phosphate, Ceteth10 Phosphate | 5.0 |
| Cetyl Alcohol | 0.25 |
| PPG-3 Benzyl Ether Myristate | 5.0 |
| *Echium* Oil | 3.0 |
| Phase B | |
| Water | to 100 |
| Phase C | |
| Glycerine, Water, Butylene Glycol, Carbomer, Polysorbate-20, Palmitoyl Oligopeptide, Palmitoyl Tetrapeptide-3 | 4.0 |
| Perfume, Preservative, Colour | qs |

Method

Combine all ingredients of phase A, add phase B to phase A with stirring at 70 Deg C. Allow to cool to 40 Deg C. and add phase C with stirring. Adjust pH, if necessary, with dilute aqueous sodium hydroxide solution.

B] Lipid Compositions Useful for Increasing Collagen Synthesis in Skin Cells

The in vitro data on collagen synthesis from skin cells (either fibroblasts or keratinocytes) were obtained using the following experimental method. Human fibroblasts or keratinocytes were seeded into 24-well plates and cultured in normal media until approximately 50% confluent. Test solutions (*Echium* oil, *Calendula* oil or mixtures of the two oils) were initially prepared at 1% in dimethyl sulphoxide (DMSO) with sonification for 5 minutes. The concentrated oil solutions were serially diluted with normal media with sonification (5 minutes) before adding to the cells. The concentration of oils in media was 0.00001%, 0.0001%, or 0.001%.

Fibroblasts and keratinocytes were cultured with the oils for 3 days or 7 days (with a change of media containing oils at day 3 for 7 day cultures). The cells were fixed by addition of formaldehyde solution (3.7%) followed by washing three times with phosphate buffered saline (PBS). The collagen specific dye; Sirius red in picric acid (0.1%) was added to the wells for approximately 18 hours. Unbound dye was removed and wells washed with tap water until clear. Following drying the dye was eluted with "Destain" (0.2M NaOH in methanol 1:1) for 15 min with gentle shaking. The optical density of the eluates were measured (490 nm) using a plate reader.

Results

Collagen Production (Optical Density/490 nm) from Fibroblasts Following Incubation (3 Days) with Test Oils and DMSO Control.

| 0.00001% | | | 0.0001% | | | 0.001% | | |
|---|---|---|---|---|---|---|---|---|
| *Calendula* oil | *Echium* oil | DMSO | *Calendula* oil | *Echium* oil | DMSO | *Calendula* oil | *Echium* oil | DMSO |
| 0.1460 | 0.1560 | 0.1200 | 0.1580 | 0.1580 | 0.1240 | 0.1440 | 0.1460 | 0.1160 |
| 21.7% | 30.0% | | 27.4% | 27.4% | | 24.1% | 25.9% | |

Collagen Production (Optical Density/490 nm) from Keratinocytes Following Incubation (3 Days) with Test Oils and DMSO Control.

| 0.00001% | | | 0.0001% | | | 0.001% | | |
|---|---|---|---|---|---|---|---|---|
| *Calendula* oil | *Echium* oil | DMSO | *Calendula* oil | *Echium* oil | DMSO | *Calendula* oil | *Echium* oil | DMSO |
| 0.5365 | 0.4896 | 0.4219 | 0.5052 | 0.4635 | 0.4375 | 0.4688 | 0.4792 | 0.4427 |
| 27.2% | 16.0% | | 15.5% | 5.9% | | 5.9% | 8.2% | |

As can be seen in fibroblasts both test oils increased collagen synthesis by between 21.7%-30.0%. In keratinocytes the effect was less marked however at low concentrations both oils again increased collagen synthesis (*Calendula* oil—27.2%, *Echium* oil—16.0%).

C] Profilometry Study to Determine the Efficacy of a Cosmetic Skin Serum in Reducing Fine Lines and Wrinkles A home-use study was carried out on 22 female subjects over a six week period. Trans-epidermal water-loss (TEWL) measurements and skin impressions were taken at baseline and at the end of the six week usage period. A consumer perception questionnaire was also completed by all subjects after the six weeks of use. The aim of the study was to determine if the test material, a facial skin serum F1/1445D, was effective in reducing fine lines and wrinkles.

Skin Serum F1/1445D is a composition including 5% w/w *Echium* oil having the following formulation (all amounts are in % w/w):

| | |
|---|---|
| WATER DEIONISED | 66.61 |
| ALLANTOIN | 0.10 |
| AMIGEL GRANULATED | 0.30 |
| PHYTIC ACID | 0.02 |
| XANTHUM GUM | 0.30 |
| LACTIGLUTAMMATO | 3.00 |
| SODIUM HYALURONATE 100% | 0.06 |
| LACTIC ACID | 0.01 |
| FUCOGEL 100 | 5.00 |
| ACTISEA 100 | 5.00 |
| DL ALPHA TOCOPHEROL | 0.50 |
| AVOCADOL | 2.00 |
| BIOPHILLIC S | 2.00 |
| TEGOCARE 450 | 0.50 |
| *ECHIUM* OIL | 5.00 |
| ACTIPHYTE OF GOTU KOLA | 2.00 |
| WITCH HAZEL BPC DIST. | 2.00 |
| *Pimpinella Anisum* (Anise) Fruit Extract | 2.00 |
| *Prunus Amygdalus Dulcis* (Sweet Almond Seed Extract) | 2.00 |
| LIPOSYS.COMP.VITAMIN A&E | 0.5 |
| EUXYL K702 | 0.60 |
| K/62277 ROSEBUD FRAG. | 0.50 |

Results

The comments given by the subjects were generally positive. However, the fragrance of the serum was disliked by the majority of the panel.

Statistical Report

1. Methodology

The Medical Data Sciences Department at Inveresk, a Charles River Company, performed the statistical analysis. The statistics package SAS (v8.2) was used to perform the statistical analyses.

Profilometry and TEWL assessments were available for 22 volunteers. Readings were taken at Baseline and Week 6. The treatment was applied to the face twice daily for 6 weeks, morning and night. Casts of the skin surface and evaporimeter readings were taken from the temple area of each side of the face at Baseline and Week 6.

1.1 Statistical Methods Planned in Protocol

The primary endpoints for analysis were the changes from Baseline (pre-treatment) to Week 6 (post treatment) for each roughness parameter assessment (Sa, Sq, Sp, Sv, St, and Sz), obtained from the profilometer.

The change from Baseline to Week 6 for each roughness parameter was subjected to parametric analysis of covariance (ANCOVA) techniques using SAS procedure PRC MIXED. The ANCOVA tested the null hypothesis that the changes from Baseline to Week 6 were equal to zero. The model included terms for side (left or right temple area) and Baseline value, with subject as a random effect. The adjusted mean changes from Baseline to Week 6, the corresponding 95% confidence intervals and p-values are presented for each roughness parameter.

Exploratory analysis was undertaken to assess the influence of outliers. If assumptions for a normal distribution remained doubtful, a corresponding non-parametric approach (i.e. a generalised Wilcoxon test, applying the ranked response variable to the above analysis) was to be used.

The secondary endpoint, change from Baseline to Week 6 for TEWL, was analysed using the same technique as for the primary endpoints.

1.2 Changes from Planned Methods

Additionally, the adjusted mean changes from Baseline to Week 6, the corresponding 95% confidence intervals and p-values are presented for each roughness parameter separately by side (using the same ANCOVA model as detailed above), as there was a noticeable difference in the mean change from baseline values between the left and right temple areas for all roughness parameters.

2. Results for Week 6 Change from Baseline 2.1 Change from Baseline

TABLE I

Statistical Analysis of Profilometry and TEWL Parameters

| Parameter | Post treatment Change from Baseline | Lower 95% CI | Upper 95% CI | P-value |
|---|---|---|---|---|
| Sa (μm) | −4.3 | −6.7 | −1.9 | 0.001 |
| SA (μm)* | −4.9 | −7.0 | −2.8 | <0.001 |
| Sq (μm) | −5.9 | −9.2 | −2.6 | 0.001 |
| Sq (μm)* | −6.8 | −9.7 | −3.8 | <0.001 |
| Sp (μm) | −37.9 | −58.5 | −17.3 | <0.001 |
| Sv (μm) | −29.5 | −57.6 | −1.5 | 0.040 |
| Sv (μm)* | −36.6 | −59.2 | −14.1 | 0.003 |
| St (μm) | −67.4 | −103.7 | −31.2 | <0.001 |
| Sz (μm) | −57.5 | −79.6 | −35.5 | <0.001 |
| TEWL (g/cm²/h) | −2.8 | −3.8 | −1.9 | <0.001 |

*results after removing extreme observation

Table 1 presents the results for the roughness and TEWL parameters analysed. All roughness parameters had a statistically significant reduction from Baseline to Week 6 for TEWL, there was also found to be a statistically significant reduction from Baseline to Week 6.

The assumption of normality was satisfied for parameters Sp, St, Sz and TEWL. For the remaining parameters Sa, Sq, and Sz there was evidence of one outlier in each analysis (Panel no. 19672, right side for Sa and Sq, and panel no. 20271, left side for Sv). A secondary analysis was undertaken with the removal of the relevant outliers and the normality assumption was satisfied following the removal of outliers.

3. Results for Week 6 Change from Baseline by Side 3.1 Change from Baseline by Side There was a noticeable difference in the mean change from baseline values between the left and right temple areas for all roughness parameters. The mean difference between values from the left and right side even reached statistical significance at the 5% level for parameters Sa, Sq and Sz. Therefore Table II presents the results for the left and right temple areas separately for all roughness and TEWL parameters analysed.

TABLE II

Statistical Analysis of Profilometry and TEWL Parameters by Side

| Parameter | Temple Area | Post treatment Change from Baseline | Lower 95% CI | Upper 95% CI | P-value |
|---|---|---|---|---|---|
| Sa (μm) | Left | −6.7 | −9.7 | −3.6 | <0.001 |
| | Left* | −6.7 | −9.3 | −4.1 | <0.001 |
| | Right | −2.0 | −5.0 | 1.1 | 0.20 |
| | Right* | −3.1 | −5.8 | −0.4 | 0.024 |
| Sq (μm) | Left | −9.4 | −13.6 | −5.1 | <0.001 |
| | Left* | −9.5 | −13.0 | −5.9 | <0.001 |
| | Right | −2.4 | −6.7 | 1.8 | 0.25 |
| | Right* | −4.1 | −7.7 | −0.4 | 0.029 |
| SP (μm) | Left | −50.8 | −80.0 | −21.6 | 0.001 |
| | Right | −25.0 | −54.2 | 4.2 | 0.092 |
| Sv (μm) | Left | −42.7 | −81.2 | −4.1 | 0.031 |
| | Left* | −57.6 | −89.0 | −26.2 | <0.001 |
| | Right | −16.4 | −55.0 | 22.1 | 0.39 |
| | Right* | −15.6 | −46.3 | 15.0 | 0.31 |
| St (μm) | Left | −98.0 | −148.3 | −47.8 | <0.001 |
| | Right | −36.9 | −87.1 | 13.4 | 0.15 |
| Sz (μm) | Left | −87.4 | −115.6 | −59.9 | <0.001 |
| | Right | −27.3 | −55.2 | 0.6 | 0.055 |
| TEWL (g/cm²/h) | Left | −3.1 | −4.1 | −2.1 | <0.001 |
| | Right | −2.6 | −3.6 | −1.6 | <0.001 |

*results after removing extreme observation

All roughness parameters had a statistically significant reduction from Baseline to Week 6 for the left temple area, however this reduction was not found to be significant for the right temple area for any of the roughness parameters. For TEWL, there was found to be a statistically significant reduction from baseline to Week 6 for both temple areas.

The assumption of normality was satisfied for parameters Sp, St, Sz and TEWL. For the remaining parameters Sa, Sq and Sz there was evidence of one outlier in each analysis (Panel no. 19672, right side for Sa and Sq, and panel no. 20271, left side for Sv). A secondary analysis was undertaken with the removal of the relevant outliers, and the normality assumption was satisfied following the removal of outliers.

D] Analyses of the Effects of Lipid Formulations on Collagen 1 Content

Protocol

Lipid formulations were applied topically on EST-1000 epidermis models (Cellsystems Biotechnologie Vertrieb GmbH) as shown in FIG. 1. The models consist of primary human keratinocytes and exhibit a physiological differentiation pattern throughout the epidermal layers consisting of a basal cell layer (stratum basale), spinous (or prickle) cell layer (stratum spinosum), granular layer (stratum granulosum) and finally the cornified layer (stratum corneum). The cornified layer is responsible for the characteristic barrier capacity of the epidermis. The barrier function is used as the main quality control. The EST-1000 models are usually cultivated for 14 days at airlift conditions. To facilitate a longer time of treatment and observation skin models of 11 day airlift culture were used throughout this study.

Pre-Experimental Run Testing Collagen I ELISA

Before the start of the study, the protocol and detection system for the analyses of collagen I protein were tested using an EST-1000 model each. The skin model was untreated.

Collagen protein was secreted into the extracellular matrix (ECM). Therefore, the protein has to be extracted from the ECM. The extraction protocol involves the treatment of the skin model by pepsin and elastase. The concentration of the protein fragments released by the extraction was measured by ELISA and correlated directly to the collagen content.

Extraction Protocol

A) Pepsin Digestion
1. Cut out the membrane with the epidermis (henceforth called EST) from the insert.
2. Incubate EST in H$_2$O bidest (0.5 mL) in a 2.0 mL cup over night at 4° C.
3. Centrifuge at 10.000 rpm and 4° C. (Biofuge fresco, Heraeus) for 3 min.
4. Transfer EST into 0.1 mL pepsin buffer (0.1 mg/mL in 0.05 M acetic acid).
5. Incubate over night at 4° C. with careful shaking.
6. Centrifuge at 10.000 rpm and 4° C. (Biofuge fresco, Heraeus) for 3 min.
7. Transfer supernatant into a collection tube containing 0.1 mL buffered normal goat sera.

B) Elastase Digestion
1. incubate EST in 0.1 mL elastase buffer (0.1 mg/mL in 0.1 M Tris—0.15 M NaCl—5 mM CaCl$_2$ pH 7.8)
2. Incubate overnight at 4° C. with careful shaking.
3. Centrifuge at 10.000 rpm and 4° C. (Biofuge fresco, Heraeus) for 3 min.
4. Combine the supernatant into the collection tube from step 7 pepsin digestion.

C) Neutralisation

The pH in the combined supernatant in the collection tubes are neutralised by adding 1 M Tris buffer (1/50 of the volume of the supernatants).

D) Collagen ELISA

The above described collagen extraction protocol is adapted from the collagen I extraction protocol described in the manual of the collagen I detection kit (Chondrex Inc. #6008).

The determination of collagen I was performed following the protocol given by the producer of the collagen I detection kit (Chondrex Inc. #6008).

Gene Expression Analyses

The expression of the genes coding for collagen I was analysed by RT-PCR (reverse transcriptase polymerase chain reaction) using the Taqman gene expression assays (Applied Biosystems). The ESTs were cut from the inserts as described above. The cut ESTs were stored in RNAlater (Ambion) at 4° C. until RNA preparation. For RNA preparation the tissue was disintegrated using the Precellys (Peqlab Biotechnologie GmbH, Germany). The cells were lysed in RLT buffer (RNeasy-kit, Qiagen). The RNA was purified from these lysates by three different protocols:
1. RNeasy (Qiagen)
2. Trizol extraction (Invitrogen, standard phenol extraction protocol)
3. Chloroform extraction (standard protocol)

From the untreated EST-1000 sufficient RNA could be isolated with all three methods. The RNeasy method failed in both samples to purify RNA from ESTs treated with the test formulation. The same result was obtained using the Trizol protocol. Using the chloroform extraction (standard molecular biology protocol), RNA could be isolated also from the treated ESTs).

Consequently, all RNAs analysed by RT-PCR were purified by chloroform extraction.

Results

Figure 2:
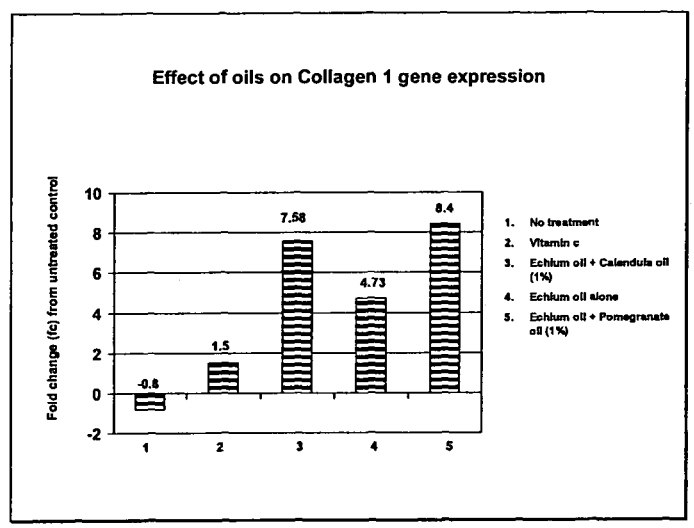
FIG. 2 is a bar graph showing the effect of various oils on collagen 1 gene expression.

The expression of the collagen I gene was induced by all treatments (see FIG. 2). In particular, a relatively high fold change was observed for *Echium* oil in combination with *Calendula* oil and for *Echium* oil in combination with pomegranate seed oil.

E] Effect of *Echium* Oil and *Calendula* Oil Containing Products on Gene Expression in the EST 1000™ Skin Model Summary Eight test oils containing *Echium* oil and *Calendula* oil, 2 commercially available cosmetic lotions[1] and 2 experimental lotions[2] were evaluated in the EST 1000™ skin model[3]. The test oil used was glyceryl tricaprylate/caprate (Crodamol GTCC, or MCT) to act as an inert carrier oil. The overall objective was to confirm earlier results showing that *Echium/Calendula* oil mixtures were synergistic in promoting collagen synthesis in skin. A number of genes involved in collagen synthesis in skin cells were analyzed using the reverse transcription-polymerase chain reaction (RT-PCR).

Notes
1. The commercially available cosmetic lotions were; "Protect and Perfect Intense Beauty Serum" (The Boots Company PLC, Nottingham England) and "Advanced Night Repair Concentrate" (Estee Lauder DIST., New York N.Y., USA). Both products carry "moisturization" or "skin repair" claims and are brand leaders.
2. Experimental lotions were fully formulated products (Formula I Cosmetic Developments Company Ltd., West Sussex UK) containing either *Echium* oil alone or a mixture of *Echium* oil plus *Calendula* oil.
3. The EST 1000™ skin model is a 3-dimensional differentiated skin-cell model or "living skin equivalent".

Formulations

The experimental lotions (referred to as Seeds #2 and Seeds #3 in Table III below) have the following composition:

| INCI NAME | Sum Of INCI FORMULA |
|---|---|
| Seeds #2 | |
| AQUA | 75.147 |
| CAPRYLIC/CAPRIC TRIGLYCERIDE | 10 |
| *ECHIUM PLANTAGINEUM* OIL | 5 |
| C12-16 ALCOHOLS | 2.48 |
| CETEARYL ALCOHOL | 1.5 |
| GLYCERIN | 0.9 |
| PALMITIC ACID | 0.76 |
| LECITHIN | 0.76 |
| SORBITOL | 0.75 |
| PHENOXYETHANOL | 0.592 |
| SODIUM PCA | 0.54 |
| INULIN LAURYL CARBAMATE | 0.5 |
| XANTHAN GUM | 0.3 |
| SCLEROTIUM GUM | 0.3 |
| SODIUM LACTATE | 0.21 |
| BENZOIC ACID | 0.096 |
| SODIUM HYALURONATE | 0.06 |
| DEHYDROACETIC ACID | 0.056 |
| PHYTIC ACID | 0.025 |
| ETHYLHEXYLGLYCERIN | 0.016 |
| POLYAMINOPROPYL BIGUANIDE | 0.008 |
| Seeds #3 | |
| AQUA | 75.147 |
| CAPRYLIC/CAPRIC TRIGLYCERIDE | 10 |
| *ECHIUM PLANTAGINEUM* OIL | 4.95 |
| C12-16 ALCOHOLS | 2.48 |

-continued

| INCI NAME | Sum Of INCI FORMULA |
|---|---|
| CETEARYL ALCOHOL | 1.5 |
| GLYCERIN | 0.9 |
| LECITHIN | 0.76 |
| PALMITIC ACID | 0.76 |
| SORBITOL | 0.75 |
| PHENOXYETHANOL | 0.592 |
| SODIUM PCA | 0.54 |
| INULIN LAURYL CARBAMATE | 0.5 |
| XANTHAN GUM | 0.3 |
| SCLEROTIUM GUM | 0.3 |
| SODIUM LACTATE | 0.21 |
| BENZOIC ACID | 0.096 |
| SODIUM HYALURONATE | 0.06 |
| DEHYDROACETIC ACID | 0.056 |
| *CALENDULA OFFICINALIS* OIL | 0.05 |
| PHYTIC ACID | 0.025 |
| ETHYLHEXYLGLYCERIN | 0.016 |
| POLYAMINOPROPYL BIGUANIDE | 0.008 |

Protocol

Treatment Scheme of EST1000

Viability Test:

20 μL of the test oils were applied on the surface of the EST1000 in triplicates. After application the ESTs were incubated over night (18 h) at 37° C., 5% $CO_2$ and 100% humidity. The visibility of EST1000 was measure by MTT-test.

Gene Expression Analyses:

20 μL of the test oils were applied on the surface of the EST1000 in triplicates. After application the ESTs were incubated over night (18 h) at 37° C., 5% $CO_2$ and 100% humidity. The epidermis was cut out of the insert and the tissues were fixed in RNAlater (Ambion) for RNA preparation. The RNA was prepared and the concentration and quality of the isolated RNA was controlled. The quality is determined by the ratio between the optical densities of the RNA at 260 and 280 nm. A ratio of more or equal 1.8 represents a good quality of RNA.

The gene expression of the three genes of interest (Col1A1, Col3A1, Col4A6) was analysed by quantitative real-time RT-PCR (Taqman).

MTT-Test

The viability of EST1000 was measured by the MIT-test which is based on the reduction of 3-4,5-dimethylthiazol-2-yl)-2,5-diphenyltetrazoliumbromid (MIT) by the mitochondrial reductases. The reduction of MTT leads to the formation of purple formazan crystals which are solved in isopropanol. The amount of formazan can be measured at 550 nm and correlates directly with the viability. The viability of the treated epidermis models is calculated as percentage of the non treated controls which are defined as 100%.

RT-PCR

The RT-PCR analyses were performed according to the Applied Biosystems protocol (Taqman). In short: 1 μg of the RNA was transcribed to cDNA which was used as template for the real-time RT-PCR with gene specific primers and probes.

Results

The master results are shown in Table III below and then separated out in the following Tables. A marked synergism, with respect to the expression of collagen1, collagen 3 and collagen 4 genes was observed, using the *Echium* oil and *Calendula* oil "model compound" mixtures. This result was also observed in the fully formulated experimental lotions.

TABLE III

| | Echium oil (%) | Calendula oil (%) | Collagen 1 | Collagen 3 | Collagen 4 |
|---|---|---|---|---|---|
| Carrier oil | | | | | |
| MCT | 0 | 0 | −10.6 | 9.5 | 0.9 |
| MCT | 0 | 0.05 | −8.2 | −37.4 | 6.7 |
| MCT | 0 | 5.0 | −6.8 | 55.7 | 3.2 |
| MCT | 5.0 | 0 | 3.0 | −3.26 | −1.8 |
| MCT | 4.95 | 0.05 | 23.5 | 609.4 | 6.6 |
| Product | | | | | |
| Estee Lauder | 0 | 0 | −32.5 | −8.2 | −60.9 |
| Boots No. 7 | 0 | 0 | −19.5 | 7.1 | 2.6 |
| Seeds #2 | 5 | 0 | 20.9 | 423.8 | −2.1 |
| Seeds #3 | 4.95 | 0.05 | 38.8 | 693.3 | 7.2 |

Genes

Collagen 1A1 gene encodes the most abundant protein in skin, tendon and bone, it is the end product when tissue heals by repair.

Collagen 3A1 produced in young fibroblasts before the production of stronger type 1 collagen.

Collagen 4A6 the key protein in basal lamina. The gene encodes one of the six subunits of type 4 collagen.

Figure 3:
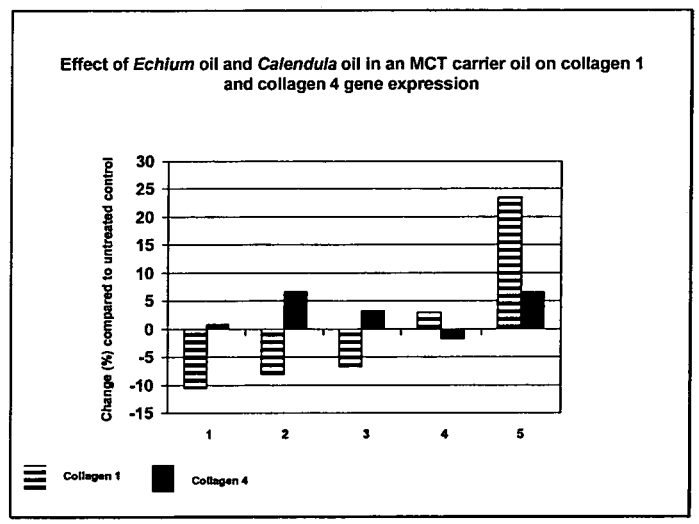
FIG. 3 is a bar graph showing the effect of various oils on collagen 1 and collagen 4 gene expression.

E1] Effect of Oils in MCT Carrier Oil on Change of Collagen 1 and Collagen 4 Gene Expression Four oils were evaluated: the carrier oil (Crodamol GTCC) alone, carrier oil containing *Calendula* oil (0.05%), carrier oil containing *Echium* oil (5%), carrier oil containing *Echium* oil (4.95%) and *Calendula* oil (0.05%). The results are shown in Table IV below and graphically in FIG. 3.

TABLE IV

Effect of oils in MCT carrier oil on collagen 1 and collagen 4 gene expression

| Oil number | Oil | Collagen 1 Change (%) from untreated control | Collagen 4 Change (%) from untreated control |
|---|---|---|---|
| 1 | MCT oil alone | −10.6 | 0.9 |
| 2 | MCT oil + *Calendula* oil (0.05%) | −8.2 | 6.7 |
| 3 | MCT oil + *Calendula* oil (5%) | −6.8 | 3.2 |
| 4 | MCT oil + *Echium* oil (5%) | 3.0 | −1.8 |
| 5 | MCT oil + *Echium* oil (4.95%) + *Calendula* oil (0.05%) | 23.5 | 6.6 |

Figure 4:
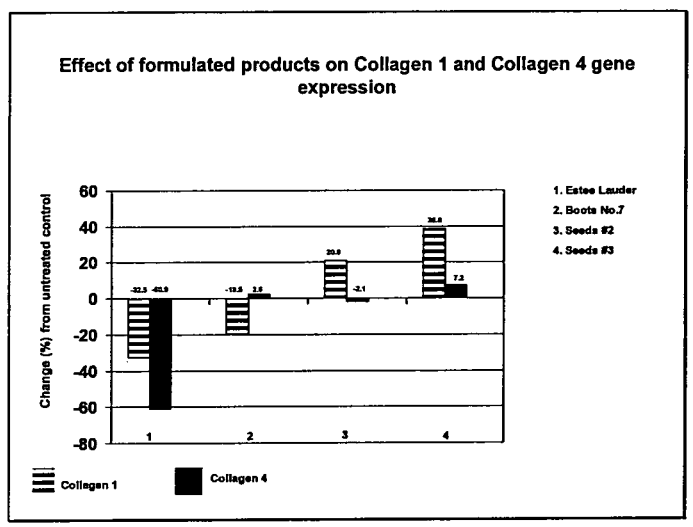
FIG. 4 is a bar graph showing the effect of various formulated products on collagen 1 and collagen 4 gene expression.

E2] The Effect of Applied Commercial Products on Collagens 1, 3 and 4 Gene Expression in the EST1000™ Skin Model Two commercially available skin-care products Estee Lauder's "Advanced Night Repair Concentrate" and "No7 Protect & Perfect Intense Beauty Serum" from the Boots Company. Two experimental, fully formulated, lotions were tested; Seeds #2 containing *Echium* oil as the bioactive lipid and Seeds #3 containing *Echium* oil (4.95%) and *Calendula* oil (0.05%). The results from these tests on Collagens 1 and 4 are shown Table V below and graphically in FIG. 4:

TABLE V

Effect of formulated products on Collagen 1 and Collagen 4 gene expression

| Number | Product | Collagen 1 Change (%) From untreated control | Collagen 4 Change (%) from untreated control |
|---|---|---|---|
| 1 | Estee Lauder | −32.5 | −60.9 |
| 2 | Boots No. 7 | −19.5 | 2.6 |
| 3 | Seeds #2 (containing *Echium* oil 5%) | 20.9 | −2.1 |
| 4 | Seeds #3 (containing *Echium* oil 4.95% plus *Calendula* oil 0.05%) | 38.8 | 7.2 |

Figure 5:
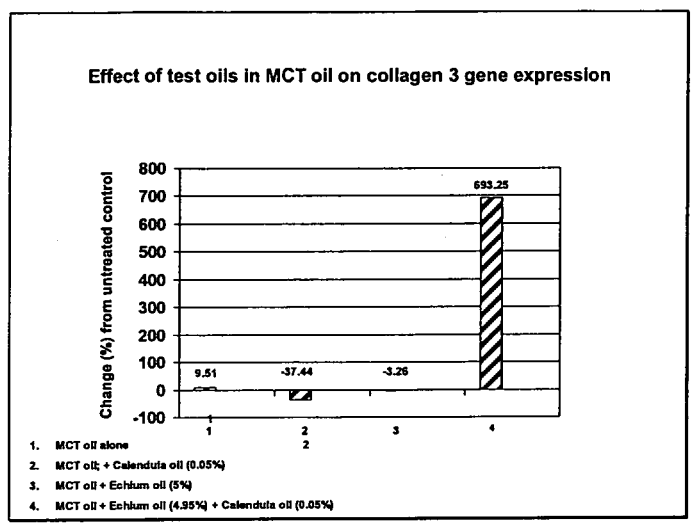
FIG. 5 is a bar graph showing the effect of various test oils on collagen 3 gene expression.
Figure 6:
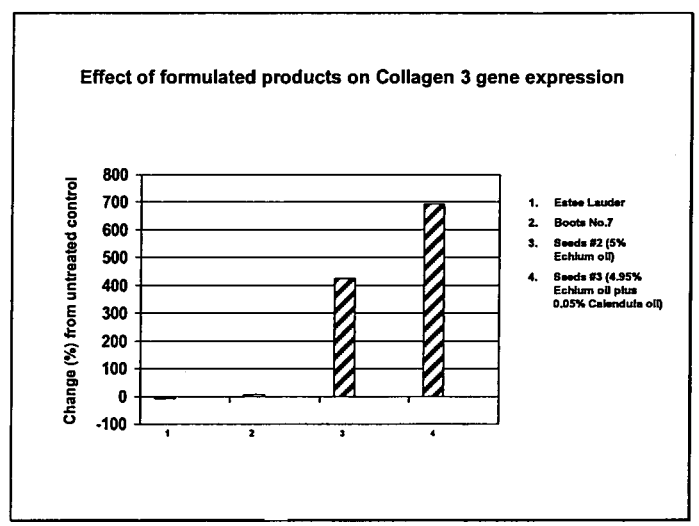
FIG. 6 is a bar graph showing the effect of various formulated products on collagen 3 gene expression.

The results of the above tests on Collagen 3 are shown in Table VI below and graphically in FIG. 5:

TABLE VI

Effect of formulated products on Collagen 3 gene expression

| Oil number | Product | Collagen 3 Change (%) from untreated control |
|---|---|---|
| 1 | Estee Lauder | −8.23 |
| 2 | Boots No. 7 | 7.09 |
| 3 | Seeds #2 Containing *Echium* oil (5%) | 423.75 |
| 4 | Seeds #3 Containing *Echium* oil (5%) plus *Calendula* oil (0.05%) | 693.25 |

The invention claimed is:

1. A topical composition for reducing visible signs of aging, reducing trans-epidermal water loss, and/or healing wounds in a human or animal body, said topical composition comprising:

an oil extracted from *Echium* seeds in an amount from 4% to 10% w/w of the composition, wherein the oil comprises stearidonic acid or an ester thereof having pro-collagen effects, and a conjugated octadecatrienoic acid or an ester thereof in an amount from 0.005% to 1% w/w of the composition, wherein the conjugated octadecatrienoic acid or an ester thereof enhances the pro-collagen effects of said stearidonic acid or ester thereof, and wherein the octadecatrienoic acid is selected from the group consisting of catalpic acid, a-eleostearic acid, punicic acid, esters thereof, and combinations thereof.

2. The topical composition as claimed in claim 1, wherein said conjugated octadecatrienoic acid is extracted from *Catalpa ovata, Aleurites fordii*, and *Punica granatum* respectively.

3. The topical composition as claimed in claim 1, additionally comprising a physiologically acceptable carrier.

4. A method of reducing visible signs of aging of human or animal skin in need thereof comprising applying to said skin an effective amount of the topical composition according to claim 1 in combination with a physiologically acceptable carrier.

5. A method of healing wounds in a human or animal body in need thereof comprising applying to the locus of the wound an effective amount of the topical composition according to claim 1 in combination with a physiologically acceptable carrier.

6. A method of reducing trans-epidermal water loss comprising applying to the locus of the wound of a subject in need thereof an effective amount of the topical composition according to claim 1 in combination with a physiologically acceptable carrier.

* * * * *